(12) United States Patent
Kitahara et al.

(10) Patent No.: US 11,384,159 B2
(45) Date of Patent: Jul. 12, 2022

(54) B-1,3-1,6-GLUCAN POWDER, GLUCAN-CONTAINING COMPOSITION, METHOD FOR PRODUCING B-1,3-1,6-GLUCAN POWDER, INCLUSION COMPLEX, METHOD FOR PRODUCING INCLUSION COMPLEX, AND METHOD FOR RECOVERING GUEST MOLECULE

(71) Applicants: MITSUBISHI GAS CHEMICAL COMPANY, INC., Tokyo (JP); KONAN GAKUEN, Hyogo (JP)

(72) Inventors: Yoshitaka Kitahara, Tokyo (JP); Kazuya Koumoto, Hyogo (JP)

(73) Assignees: MITSUBISHI GAS CHEMICAL COMPANY, INC., Tokyo (JP); KONAN GAKUEN, Hyogo (JP)

( * ) Notice: Subject to any disclaimer, the term of this patent is extended or adjusted under 35 U.S.C. 154(b) by 27 days.

(21) Appl. No.: 16/754,952

(22) PCT Filed: Oct. 10, 2018

(86) PCT No.: PCT/JP2018/037651
§ 371 (c)(1),
(2) Date: Apr. 9, 2020

(87) PCT Pub. No.: WO2019/073989
PCT Pub. Date: Apr. 18, 2019

(65) Prior Publication Data
US 2020/0231709 A1    Jul. 23, 2020

(30) Foreign Application Priority Data

Oct. 12, 2017    (JP) .............................. JP2017-198297

(51) Int. Cl.
*C08B 37/00* (2006.01)
*A61K 31/716* (2006.01)
*A23L 33/125* (2016.01)

(52) U.S. Cl.
CPC ......... *C08B 37/0024* (2013.01); *A23L 33/125* (2016.08); *A61K 31/716* (2013.01)

(58) Field of Classification Search
CPC .................................................. C08B 37/0024
See application file for complete search history.

(56) References Cited

FOREIGN PATENT DOCUMENTS

| CN | 103 800 916 A | 5/2014 |
|---|---|---|
| JP | 2005-307150 | 11/2005 |
| JP | 2007-267718 | 10/2007 |
| JP | 2007-319150 | 12/2007 |
| JP | 2009-060895 | 3/2009 |
| JP | 2011-132223 | 7/2011 |
| JP | 2014-193967 | 10/2014 |
| JP | 2016-113381 | * 6/2016 |
| JP | 2016-183120 | 10/2016 |

OTHER PUBLICATIONS

Ansari, S. et al., Molecules, "Evaluation of Rheological Properties and Swelling Behavior of Sonicated Scleroglucan Samples", 2012, vol. 17, pp. 2283-2297 (Year: 2012).*
Hirabayashi, K. et al., World J. Microbiol. Biotechnol., "Characterization and enzymatic hydrolysis of hydrothermally treated beta-1,3-1,6-glucan from Aureobasidium pullulans", 2016, vol. 32, issue 206, 7 pages (Year: 2016).*
Jantarat, C. et al., Tropical Journal of Pharmaceutical Research, "Curcumin-Hydroxypropyl-beta-Cyclodextrin Inclusion Complex Preparation Methods: Effect of Common Solvent Evaporation, Freeze Drying, and pH Shift on Solubility and Stability of Curcumin", 2014, vol. 13, No. 8, pp. 1215-1223 (Year: 2014).*
Suzuki, Toshio et al., English translation of JP2016-113381, 53 pages (Year: 2016).*
Stahmann, K.P. et al., Structural properties of native and sonicated cinerean, a beta-(1-->3) (1-->6)-D-glucan produced by Botrytis cinerea., Carbohydrate Research, vol. 266, No. 1, Jan. 3, 1995, pp. 115-128.
Official Communication ( ISR/210) dated Jan. 8, 2019 in International Patent Application No. PCT/JP2018/037651, and English translation thereof.
Official Communication ( IPRP/237) dated Jan. 8, 2019 in International Patent Application No. PCT/JP2018/037651, and English translation thereof.
Extended European Search Report issued in EPO Patent Application No. 18865852.0, dated Jun. 30, 2021.

* cited by examiner

*Primary Examiner* — Bahar Craigo
(74) *Attorney, Agent, or Firm* — Greenblum & Bernstein, P.L.C.

(57) ABSTRACT

Provided are a β-1,3-1,6-glucan powder having high solubility in water, a glucan-containing composition using the powder or the like, a method for producing the β-1,3-1,6-glucan powder, an inclusion complex, a method for producing the inclusion complex, and a method for recovering a guest molecule. The β-1,3-1,6-glucan powder has a saturation solubility in water at 25° C. of from 1.0 to 20.0 % by mass. The β-1,3-1,6-glucan powder is such that in a particle size distribution of β-1,3-1,6-glucans, determined by subjecting the β-1,3-1,6-glucan powder to dynamic light scattering measurements, a particle size of a peak representing a largest volume fraction is in a range from 5 nm to 15 nm, and a volume fraction of a peak outside of the particle size range from 5 nm to 15 nm is 30 % or less of the volume fraction of the peak having the largest volume fraction.

14 Claims, 5 Drawing Sheets

β-1,3-1,6-GLUCAN POWDER, GLUCAN-CONTAINING COMPOSITION, METHOD FOR PRODUCING β-1,3-1,6-GLUCAN POWDER, INCLUSION COMPLEX, METHOD FOR PRODUCING INCLUSION COMPLEX, AND METHOD FOR RECOVERING GUEST MOLECULE

TECHNICAL FIELD

The present invention relates to a β-1,3-1,6-glucan powder, a glucan-containing composition, a method for manufacturing a β-1,3-1,6-glucan powder, an inclusion complex, a method for producing an inclusion complex, and a method for recovering a guest molecule.

In particular, the present invention relates to a β-1,3-1,6-glucan powder with high solubility in water.

BACKGROUND ART

It is known that microorganisms such as *Aureobasidium* sp. produce β-D glucans. β-D glucans have been suggested to have an anticancer action and an immunostimulatory action, and are useful as a health food ingredient.

β-D glucans, because of its structure, generally take on a rigid triple helical structure in an aqueous solution, and therefore the mean-square radius of gyration is great. Thus, microorganism culture solutions containing β-glucans produced extracellularly exhibit high viscosity and are difficult to purify. Without exception, even a culture solution of *Aureobasidium* sp. microorganisms contains β-1,3-1,6-D-glucans produced extracellularly, and therefore the viscosity is high, and it is extremely difficult to remove bacterial cells from the culture solution, and recover and purify the β-1,3-1,6-D-glucans.

Based on such circumstances, Patent Document 1 discloses a method for producing purified β-D-glucans, the method including: a first step of adjusting a microorganism culture solution or a ground microorganism solution, containing β-D-glucans, to a pH of 12 or higher; a second step of removing microorganisms or insoluble contaminants to obtain a supernatant; and a third step of removing all or some of the contaminants of lower molecular weight than the β-D-glucans through ultrafiltration of the supernatant under alkaline conditions. Patent Document 1 also describes that a highly transparent β-D-glucan can be obtained by such a production method.

CITATION LIST

Patent Document

Patent Document 1: JP 2007-267718 A

SUMMARY OF INVENTION

Technical Problem

Patent Document 1 describes that an alkali is added to a β-1,3-1,6-glucan culture solution, and diatomaceous earth is added thereto, after which the mixture is filtered and neutralized with an aqueous citric acid solution, and then lyophilized.

However, the present inventors studied the above Patent Document 1 and found that the β-1,3-1,6-glucan powder that is obtained exhibits low solubility in water.

Thus, an object of the present invention is to solve the problems described above, and to provide a β-1,3-1,6-glucan powder having high solubility in water, a glucan-containing composition using the powder or the like, a method for producing the β-1,3-1,6-glucan powder, an inclusion complex, a method for producing the inclusion complex, and a method for recovering a guest molecule.

Solution to Problem

The present inventors diligently conducted research on the basis of the above-mentioned problems, and as a result, discovered that the problems described above can be solved by removing β-1,3-1,6-glucans having a large particle size from a raw material composition containing water and β-1,3-1,6-glucans, and then lyophilizing and/or spray drying β-1,3-1,6-glucans to thereby form a powder.

More specifically, the problems described above are solved by the following means <1>, and preferably by the following means <2> to <15>.

<1> A β-1,3-1,6-glucan powder with a saturation solubility in water at 25° C. of from 1.0 to 20.0% by mass.

<2> The β-1,3-1,6-glucan powder according to <1>, wherein in a particle size distribution of β-1,3-1,6-glucans, determined by subjecting the β-1,3-1,6-glucan powder to dynamic light scattering measurements, a particle size of a peak representing a largest volume fraction is in a range from 5 nm to less than 100 nm, and a volume fraction of a peak outside of the particle size range from 5 nm to less than 100 nm is 30% or less of the volume fraction of the peak having the largest volume fraction.

<3> A β-1,3-1,6-glucan powder wherein,
in a particle size distribution of β-1,3-1,6-glucans, determined by subjecting the β-1,3-1,6-glucan powder to dynamic light scattering measurements, a particle size of a peak representing a largest volume fraction is in a range from 5 nm to 15 nm, and a volume fraction of a peak outside of the particle size range from 5 nm to 15 nm is 30% or less of the volume fraction of the peak having the largest volume fraction.

<4> A glucan-containing composition containing the β-1,3-1,6-glucan powder described in any one of <1> to <3> and water.

<5> A glucan-containing composition containing water and β-1,3-1,6-glucans, wherein
the β-1,3-1,6-glucans are dissolved at a ratio of from 1.0 to 20.0% by mass in water; and
in a particle size distribution of the β-1,3-1,6-glucans, determined by subjecting the composition to dynamic light scattering measurements, a particle size of a peak representing a largest volume fraction is in a range from 5 nm to less than 100 nm, and a volume fraction of a peak outside of the particle size range from 5 nm to 15 nm is 30% or less of the volume fraction of the peak having the largest volume fraction.

<6> A β-1,3-1,6-glucan-containing composition containing water and β-1,3-1,6-glucans, wherein,
in a particle size distribution of the β-1,3-1,6-glucans, determined by subjecting the glucan-containing composition to dynamic light scattering measurements, a particle size of a peak representing a largest volume fraction is in a range from 5 nm to 15 nm, and a volume fraction of a peak outside of the particle size range from 5 nm to 15 nm is 30% or less of the volume fraction of the peak having the largest volume fraction.

<7> The glucan-containing composition according to any one of <4> to <6>, wherein the composition has a transmittance of light with a wavelength of 660 nm at 25° C. of 70% or more.

<8> A method for producing a β-1,3-1,6-glucan powder, the method including lyophilizing and/or spray drying a pre-composition containing water and β-1,3-1,6-glucans, the pre-composition being such that in a particle size distribution of the β-1,3-1,6-glucans, determined by subjecting the pre-composition to dynamic light scattering measurements, a particle size of a peak representing a largest volume fraction is in a range from 10 nm to less than 1000 nm, and a volume fraction of a peak for a particle size of 1000 nm or more is 10% or less of the volume fraction of the peak having the largest volume fraction.

<9> The method for producing a β-1,3-1,6-glucan powder according to <8>, wherein the pre-composition is obtained by removing, through centrifugation, filtration, or dialysis, β-1,3-1,6-glucans having a large particle size from a raw material composition containing β-1,3-1,6-glucans.

<10> The method for producing a β-1,3-1,6-glucan powder according to <8> or <9>, wherein the β-1,3-1,6-glucan powder is the β-1,3-1,6-glucan powder described in any one of <1> to <3>.

<11> An inclusion complex in which a guest molecule is enveloped in β-1,3-1,6-glucan derived from at least one of the β-1,3-1,6-glucan powder described in any one of <1> to <3> and the glucan-containing composition described in any one of <4> to <6>.

<12> The inclusion complex according to <11>, wherein the inclusion complex is in powder form.

<13> A method for producing an inclusion complex, the method including enveloping a guest molecule using at least one of the β-1,3-1,6-glucan powder described in any one of <1> to <3> and the glucan-containing composition described in any one of <4> to <7>.

<14> The method for producing an inclusion complex according to <13>, wherein the inclusion complex is in powder form.

<15> A method for recovering a guest molecule, the method including enveloping a guest molecule using at least one of the β-1,3-1,6-glucan powder described in any one of <1> to <3> and the glucan-containing composition described in any one of <4> to <7>.

Advantageous Effects of Invention

According to the present invention, a β-1,3-1,6-glucan powder having high solubility in water, a glucan-containing composition using the powder or the like, a method for producing the β-1,3-1,6-glucan powder, an inclusion complex, a method for producing the inclusion complex, and a method for recovering a guest molecule can be provided.

DESCRIPTION OF EMBODIMENTS

Figure 1:
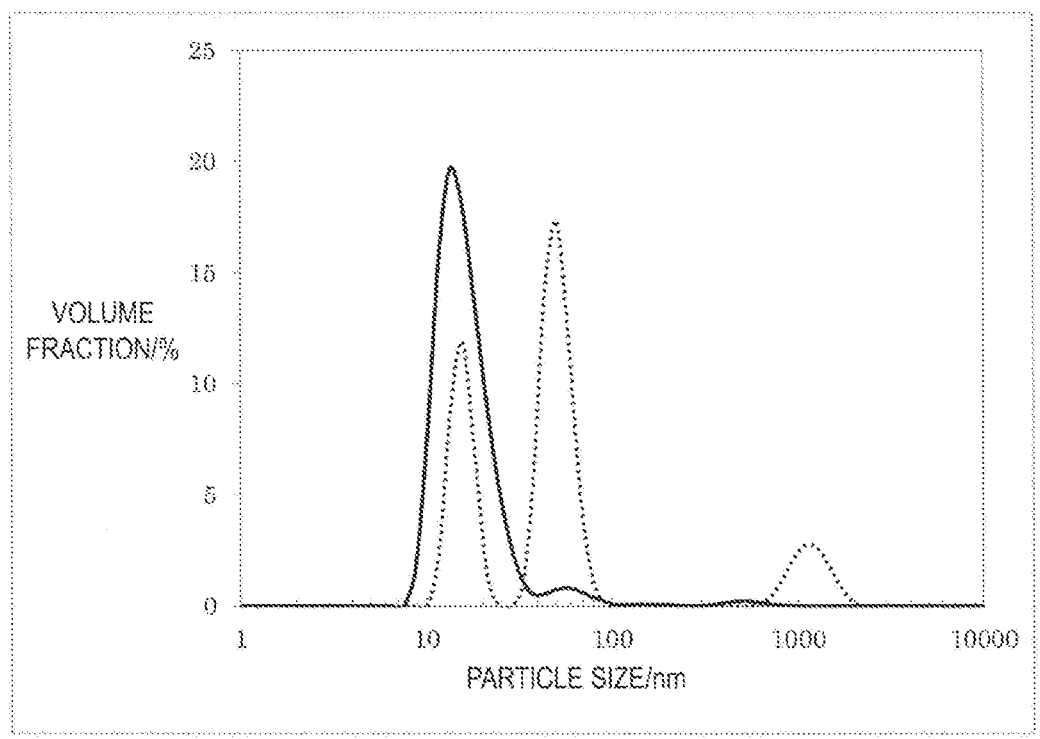
FIG. 1 is a graph illustrating a distribution of particle sizes of β-1,3-1,6-glucan prepared in the examples prior to lyophilization.

The contents of the present invention will be described in detail below. Note that, in the present specification, "from . . . to . . . " is used to mean that the given numerical values are included as the lower limit value and the upper limit value, respectively.

The term solution in the present invention refers to a mixture in a liquid state, composed of two or more substances. Therefore, a composition, etc. in which β-1,3-1,6-glucan particles or inclusion complexes are dispersed in a solvent such as water are also included in the term solution in the present invention.

β-1,3-1,6-Glucan Powder

A first aspect of a β-1,3-1,6-glucan powder of the present invention has a saturation solubility at 25° C. from 1.0 to 20.0% by mass when dissolved in water. As shown in the examples described in detail below, even when a β-1,3-1,6-glucan powder obtained by a known method is dissolved in water, such a high saturation solubility is not obtained. However, when investigated by the present inventors, it was discovered that a β-1,3-1,6-glucan powder having high saturation solubility can be produced by forming a powdering from a solution (pre-composition) obtained by removing β-1,3-1,6-glucans having a large particle size from a solution (raw material composition) containing water and β-1,3-1,6-glucans. When the solubility in water can be increased in this manner, the inclusion complex is more easily manufactured.

Furthermore, the dissolution of β-1,3-1,6-glucan in the present invention refers to a state in which precipitates are not produced and the glucan concentration of the supernatant does not change even when the centrifugation operation is repeated. More specifically, the dissolution is in accordance with the examples described below. Furthermore, in the present invention, the saturation solubility of β-1,3-1,6-glucan refers to the solubility of β-1,3-1,6-glucan at which β-1,3-1,6-glucans have dissolved at the maximum concentration without the generation of precipitates even when a β-1,3-1,6-glucan powder is added to water and stirred and a centrifugation operation is repeated as described above. More specifically, the saturation solubility is in accordance with the examples described below.

Moreover, with another aspect of the β-1,3-1,6-glucan powder of the present invention, in a particle size distribution of β-1,3-1,6-glucans, determined by subjecting the β-1,3-1,6-glucan powder to dynamic light scattering measurements, a particle size of a peak representing a largest volume fraction is in a range from 5 nm to 15 nm (preferably 8 nm or more, and preferably 13 nm or less), and a volume fraction of a peak (other peaks) outside of the particle size range from 5 nm to 15 nm is 30% or less (preferably 25% or less, more preferably 20% or less) of the volume fraction of the peak having the largest volume fraction. The matter of the volume fraction of the other peaks being 30% or less of the volume fraction of the peak having the largest volume fraction means that [(volume fraction of other peaks)/(volume fraction of the largest peak)]×100 (unit %) is 30% or less. Similar considerations are made below. The volume fraction is measured by a method described in the examples.

Raw Material β-1,3-1,6-Glucan

The raw material β-1,3-1,6-glucan used in the production of the β-1,3-1,6-glucan powder of the present invention is a polysaccharide that is widely present in nature, such as in mushrooms, seaweed, and bacteria.

β-1,3-1,6-glucan is one type of β-glucan, and is a polysaccharide constituted from glucose. The molecular structure of β-1,3-1,6-glucan is a chain structure in which numerous glucoses are bound by β-1,3-glucoside bonds, and it is presumed that β-1,6-glucoside side chains with different introduction rates depending on the type are partially introduced. It is also presumed that in the natural state, in water, three β-1,3-1,6-glucan molecular main chains mutually affect each other to form a triple-stranded helical structure.

With the β-1,3-1,6-glucan used in the present invention, the degree of branching, which is the ratio of the number of β-1,6 bonds in the side chain to the number of β-1,3 bonds in the main chain, is ordinarily from 1 to 100%, preferably from 5 to 100%, and more preferably from 30 to 100%.

The matter of the β-1,3-1,6-glucan having the above-mentioned degree of branching can be confirmed from the release of glucose and gentiobiose as decomposition products when β-1,3-1,6-glucan is hydrolyzed by exo-type β-1,3-glucanase (Kitalase M, available from K.I. Chemical Industry Co., Ltd.), and from the integration ratio of NMR (General Editor Tadayuki IMANAKA, Major Evolution of Microorganism Use, 1012-1015, NTS Inc. (2002)).

The β-1,3-1,6-glucan, which is a raw material for the β-1,3-1,6-glucan powder of the present invention, can be produced by culturing and fractioning bacteria or extracting from mushrooms, seaweed, or the like. Specific examples of the β-1,3-1,6-glucan that serves as a raw material for the β-1,3-1,6-glucan powder of the present invention include β-1,3-1,6-glucan derived from black yeast (*Aureobasidium pullulans*), β-1,3-1,6-glucan derived from *Sparassis crispa*, β-1,3-1,6-glucan derived from baker's yeast, β-1,3-1,6-glucan derived from *Agaricus subrufescens*, lichenin derived from Iceland moss, schizophyllan derived from Schizophyllum commune, laminarin derived from kelp, scleroglucans derived from sclerotium, lentinan derived from Lentinus edodes, krestin derived from Trametes versicolor, packiman derived from mushrooms, curdlan derived from Agrobacterium, grifolan derived from *Grifola frondosa*, zymosan extracted from yeast, callose contained in plant cell walls, and paramylon derived from euglena.

As a method for producing β-1,3-1,6-glucan, which serves as a raw material for β-1,3-1,6-glucan powder, the description of paragraphs [0025] and [0026] of JP 2014-193967 A can be referenced, the content of which is incorporated herein.

Preferably, insoluble matter, culturing raw materials, and proteins, etc. are removed from the raw material β-1,3-1,6-glucan obtained from the above-described bacteria or the like. Specifically, these substances are preferably removed by centrifugation, filtration, or dialysis. The weight average molecular weight of the β-1,3-1,6-glucan after the removal of such contaminants is preferably from 5000 to 20000000.

The β-1,3-1,6-glucan after removal of the contaminants may also be reduced in molecular weight. By reducing the molecular weight, multi-point interactions occurring amongst the molecular main chains of the β-1,3-1,6-glucan are weakened, and the solubility of β-1,3-1,6-glucan in water increases. Another advantage is that the formation of β-1,3-1,6-glucans with a large particle size is less likely to occur. In the reduction of the molecular weight, it is preferable that the weight average molecular weight of the (β-1,3-1,6-glucan is not greater than 200000, and more preferably not greater than 80000. The lower limit is the molecular weight required for β-1,3-1,6-glucan to form a triple-stranded helical structure, and for example, is preferably 2000 or more, and more preferably 3000 or more. The molecular weight of the β-1,3-1,6-glucan is preferably reduced by ultrasonic degradation, acid hydrolysis, and enzymatic hydrolysis using endo-type β-1,3-glucanase, and the like.

The raw material β-1,3-1,6-glucan from which contaminants have been removed may be temporarily powdered through lyophilization, etc., or subsequent operations may be performed without powdering.

The above-mentioned raw material β-1,3-1,6-glucan from which the contaminants have been removed is preferably alkali modified. Through alkali modification, the β-1,3-1,6-glucan with the triple-stranded helical structure can be formed into a single strand, for example. Furthermore, the alkali modified β-1,3-1,6-glucan is preferably neutralized. A β-1,3-1,6-glucan having a triple-stranded helical structure and better excelling in enveloping capacity is obtained through neutralization. The descriptions of paragraphs [0027] to [0029] of JP 2014-193967 A can be referenced for details regarding alkali modification and neutralization, the contents of which are incorporated in the present specification.

In the present invention, a raw material composition in which the raw material (β-1,3-1,6-glucan from which contaminants have been removed is dissolved in a solvent may be a β-1,3-1,6-glucan solution after alkali modification and neutralization are performed as necessary. A regenerated β-1,3-1,6-glucan solution in the examples described below is given as an example of the raw material composition of the present invention. Furthermore, the raw material composition may contain only one type of β-1,3-1,6-glucan or may contain two or more types.

Examples of the solvent in the raw material composition include water and one or more types of organic solvents, and water is preferable. The transmittance of light with a wavelength of 660 nm at 25° C. of the raw material composition is normally 98% or less, or even 80% or less. The lower limit of the transmittance is, for example, not less than 30%, and even not less than 50%. In addition, while there are differences in the maximum concentration of the β-1,3-1,6-glucan depending on the molecular weight and degree of branching of the molecular main chain of the β-1,3-1,6-glucan, when consideration is given to efficiently producing a pre-composition or a glucan-containing composition, the concentration of the β-1,3-1,6-glucan of the raw material concentration is preferably, in terms of the monomer glucose concentration, from 0.1 to 200 mmol/L, and more preferably from 1 to 150 mmol/L.

In addition, the description of paragraphs [0027] to [0035] of JP 2014-40394 A, the description of paragraphs [0026] to [0034] of JP 2014-40640 A, and the description of paragraphs [0023] to [0031] of JP 2013-227471 A, etc. can be referenced for details on the preparation of the raw material composition, the contents of which are incorporated herein.

β-1,3-1,6-glucans having a large particle size are preferably removed from the raw material composition. The method for removing β-1,3-1,6-glucans having a large particle size is not particularly limited, and examples include centrifugation, filtration, dialysis, and the like, and centrifugation is preferable. A composition containing β-1,3-1,6-glucans and water after removal of β-1,3-1,6-glucans having a large particle size from the raw material composition is referred to as a pre-composition. In the examples described below, a centrifugally regenerated β-1,3-1,6-glucan solution prior to lyophilization is given as an example of a pre-composition.

Pre-Composition

As described above, the pre-composition of the present invention is a composition obtained after removing the β-1,3-1,6-glucans having a large particle size from the raw material composition.

A first embodiment of the pre-composition is a pre-composition containing water and β-1,3-1,6-glucans, the pre-composition being such that in a particle size distribution of β-1,3-1,6-glucans, determined by subjecting the pre-composition to dynamic light scattering measurements, a particle size of a peak representing a largest volume fraction is in a range from 10 nm to less than 1000 nm, and a volume fraction of a peak for a particle size of 1000 nm or more is 10% or less of the volume fraction of the peak having the largest volume fraction. The pre-composition may contain only one type of β-1,3-1,6-glucan or may include two or more types. A second embodiment of a pre-composition is a pre-composition containing water and β-1,3-1,6-glucans, and is such that in a particle size distribution of β-1,3-1,6-glucans, determined by subjecting the pre-composition to dynamic light scattering measurements, a particle size of a peak representing a largest volume fraction is in a range of from 10 nm to less than 100 nm (preferably 12 nm or more, and preferably 80 nm or less, more preferably 60 nm or less, even more preferably 50 nm or less, yet even more 40 nm or less, and still even more preferably 30 nm or less), and a volume fraction of a peak outside of the particle size range of from 5 nm to less than 100 nm is, in each case, 30% or less (preferably 25% or less, more preferably 20% or less, and even more preferably 15% or less) of the volume fraction of the peak having the largest volume fraction.

A third embodiment of the pre-composition is a pre-composition containing water and β-1,3-1,6-glucans, and is such that in a particle size distribution of β-1,3-1,6-glucans, determined by subjecting the pre-composition to dynamic light scattering measurements, the pre-composition has only one peak with a volume fraction of 5% or more (preferably 10% or more, and more preferably 15% or more) in a range in which a particle size of the peak with the largest volume fraction is from 10 nm to less than 1000 nm.

The pre-composition of the present invention preferably satisfies at least one of the first to third embodiments, and more preferably satisfies at least the first embodiment.

The transmittance of light at a wavelength of 660 nm of the pre-composition at 25° C. is preferably 70% or higher, and more preferably 80% or higher. The upper limit of the transmittance is not particularly limited, but for example, can be set to 99% or less. In particular, the transmittance of light at a wavelength of 660 nm of the pre-composition at 25° C. is preferably at least 1% higher, and more preferably at least 2% higher, than the transmittance at a wavelength of 660 nm of the raw material composition. In addition, it is realistic for the transmittance of light at a wavelength of 660 nm of the pre-composition at 25° C. to be up to 20% higher than the transmittance at a wavelength of 660 nm of the raw material composition.

In addition, while there are differences in the maximum concentration of the β-1,3-1,6-glucan in the pre-composition depending on the molecular weight and degree of branching of the molecular main chain of the β-1,3-1,6-glucan, when consideration is given to efficiently producing a glucan-containing composition, the concentration of the β-1,3-1,6-glucans in the pre-composition is preferably, in terms of the monomer glucose concentration, from 30 to 60 mmol/L (from 0.49 to 0.97% by mass).

β-1,3-1,6-Glucan Powder and Production Method Thereof

In the present invention, the desired β-1,3-1,6-glucan powder can be produced by pulverizing the pre-composition. The β-1,3-1,6-glucan powder may include only one type of β-1,3-1,6-glucan or may contain two or more types.

Examples of the method for forming a powder include lyophilization, spray drying, electrospinning, re-precipitation, recrystallization, and concentration to dryness, and the method is preferably at least one of lyophilization or spray drying, and is more preferably lyophilization.

That is, the present invention discloses a method for producing at β-1,3-1,6-glucan powder, the method including subjecting the pre-composition to at least one of lyophilization or spray drying. In the present invention, solubility is improved, and the particle size of the β-1,3-1,6-glucan can be made smaller by powdering the pre-composition through lyophilization or the like.

The spray drying method is preferably performed at an inlet temperature of from 50 to 200° C. and an outlet temperature of from 30 to 100° C.

Furthermore, according to the method for producing a β-1,3-1,6-glucan powder of the present invention, the β-1,3-1,6-glucan powder can be adjusted such that a particle size of a peak representing the largest volume fraction in a particle size distribution of β-1,3-1,6-glucans, determined by subjecting the β-1,3-1,6-glucan powder (measured after dissolving it in distilled water) to dynamic light scattering measurements, is at least 3 nm (preferably from 3 to 7 nm, and more preferably from 3 to 5 nm) smaller than a particle size of a peak having the largest volume fraction in a particle size distribution of β-1,3-1,6-glucans, determined by subjecting the pre-composition to dynamic light scattering measurements.

Specifically, in one embodiment of the β-1,3-1,6-glucan powder of the present invention, the saturation solubility at 25° C. when dissolved in water is from 1.0 to 20.0% by mass. The lower limit of the saturation solubility is preferably 3.0% by mass or more, and more preferably 4.0% by mass or more. The upper limit of the saturation solubility is not particularly limited, but, for example, is such that the required performance is sufficiently satisfied even at 15.0% by mass or less.

In particular, the saturation solubility can be set, for example, to 9.0% by mass or more by setting the weight average molecular weight of the β-1,3-1,6-glucan powder of the present invention to 100000 or less, and furthermore to 80000 or less.

The β-1,3-1,6-glucan powder of the present invention is preferably such that in a particle size distribution of β-1,3-1,6-glucan determined by dynamic light scattering, a particle size of a peak with the largest volume fraction is in a range of from 5 nm to less than 100 nm (preferably 8 nm or more, and preferably 60 nm or less, more preferably 30 nm or less, even more preferably 20 nm or less, and yet even more preferably 15 nm or less), and a volume fraction of a peak outside of the particle size range from 5 nm to less than 100 nm is 30% or less (preferably 25% or less, and more preferably 20% or less) of the volume fraction of the peak having the largest volume fraction. That is, in the present invention, the particle size of the β-1,3-1,6-glucan can be reduced by powdering the pre-composition through lyophilization or the like.

The weight average molecular weight (Mw) of the β-1,3-1,6-glucan powder of the present invention is preferably 5000 or more, and more preferably 10000 or more. Moreover, the upper limit of the Mw is preferably 20000000 or less. The Mw at or above the lower limit described above allows the guest molecules to be more appropriately enveloped. Furthermore, the Mw at or below the upper limit described above can effectively suppress extremely high viscosity of a liquid containing the β-1,3-1,6-glucan.

The dissolution ratio at 25° C. of the β-1,3-1,6-glucan powder of the present invention (percentage of the β-1,3-1, 6-glucan powder that is dissolved, units: % by mass) can be 30% by mass or higher, 50% by mass or higher, and 70% by mass or higher in water at 25° C. The upper limit of the dissolution ratio is ideally 100% by mass, but under conditions of lyophilization or spray drying, water of crystallization that is contained also affects the dissolution ratio, and thus 99% by mass or less is realistic.

Glucan-Containing Composition

The glucan-containing composition of the present invention is a composition containing the β-1,3-1,6-glucan powder of the present invention and water. That is, the glucan-containing composition contains a β-1,3-1,6-glucan solution with a smaller particle size obtained by powdering and subsequent re-dissolution. In the below-described examples, a centrifugally regenerated β-1,3-1,6-glucan solution after lyophilization is given as an example of a glucan-containing composition.

A first embodiment of the glucan-containing composition of the present invention is a glucan-containing composition containing water and β-1,3-1,6-glucan, obtained by dissolving β-1,3-1,6-glucans at a proportion of from 1.0 to 20.0% by mass in water, and is such that in a particle size distribution of β-1,3-1,6-glucans, determined by subjecting the glucan-containing composition to dynamic light scattering measurements, a particle size of a peak with the largest volume fraction is in a range of from 5 nm to less than 100 nm (preferably 8 nm or more, and preferably 60 nm or less, more preferably 30 nm or less, even more preferably 20 nm or less, and yet even more preferably 15 nm or less), and a volume fraction of a peak outside of the particle size range of from 5 nm to less than 100 nm is 30% or less (preferably 25% or less, and more preferably 20% or less) of the volume fraction of the peak having the largest volume fraction.

A second embodiment of the glucan-containing composition of the present invention is a glucan-containing composition containing water and β-1,3-1,6-glucans, and is such that in a particle size distribution of β-1,3-1,6-glucans, determined by subjecting the glucan-containing composition to dynamic light scattering measurements, a particle size of a peak representing a largest volume fraction is in a range of from 5 nm to 15 nm (preferably 8 nm or higher, and preferably 13 nm or less), and a volume fraction of a peak outside of the particle size range of from 5 nm to less than 100 nm is 30% or less (preferably 25% or less, and more preferably 20% or less) of the volume fraction of the peak having the largest volume fraction. For example, when β-1,3-1,6-glucan derived from *Aureobasidium pullulans* is used, such a glucan-containing composition is easily obtained.

A third embodiment of a glucan-containing composition of the present invention is a glucan-containing composition containing water and β-1,3-1,6-glucan, and is such that a particle size of a peak representing the largest volume fraction in a particle size distribution of β-1,3-1,6-glucan determined by dynamic light scattering measurements, is at least 3 nm (preferably from 3 to 7 nm, and more preferably from 3 to 5 nm) smaller than a particle size of a peak having the largest volume fraction in a particle size distribution of β-1,3-1,6-glucans, determined by subjecting the pre-composition to dynamic light scattering measurements.

In the particle size distribution of β-1,3-1,6-glucans, determined by subjecting the glucan-containing composition of the present invention to dynamic light scattering measurements, a volume fraction of the particle size of the peak having the largest volume fraction is preferably 10% or higher, and more preferably 15% or higher. The upper limit is preferably set to be high, and for example, is such that the required performance is satisfied even at 25% or less, and furthermore, even at 20% or less.

In addition, since the β-1,3-1,6-glucan powder of the present invention has high solubility in water, the transmittance of light at a wavelength 660 nm at 25° C. of the glucan-containing composition of the present invention can be set to 70% or higher. Furthermore, the transmittance can also be set to 80% or higher, and particularly can be set to 83% or higher.

Moreover, the saturation concentration at 25° C. as the concentration of the β-1,3-1,6-glucan in the glucan-containing composition of the present invention is, in terms of the monomer glucose concentration, preferably from 300 to 650 mmol/L.

Furthermore, the weight average molecular weight and dispersivity of the β-1,3-1,6-glucans in the glucan-containing composition of the present invention is preferably in the same range as the weight average molecular weight and dispersivity of the β-1,3-1,6-glucan powder of the present invention.

Envelopment

It is known that in strongly alkaline solutions or in aprotic polar solvents such as dimethyl sulfoxide (DMSO), the triple-stranded helical structure of β-1,3-1,6-glucan is unraveled, and the β-1,3-1,6-glucan dissociates into single-stranded, random coil structures. It is also known that when the solution is neutralized or diluted/dialyzed from a state in which the β-1,3-1,6-glucan has been unraveled into a single-stranded, random coil structure by the strongly alkaline solution or DMSO solvent, the β-1,3-1,6-glucan returns once again to the original triple-stranded state. When other molecules are also present in the process of returning to the original triple-stranded state from the state of being unraveled into a single-stranded, random coil structure, the other molecules can be incorporated into the triple-stranded structure. That is, β-1,3-1,6-glucan acts as an inclusion host, and another molecule can be enclosed as an inclusion guest.

In addition, when the β-1,3-1,6-glucan returns from the state of being unraveled into a single-stranded, random coil structure, to the original triple-stranded state without the coexistence of other molecules, a β-1,3-1,6-glucan in which the triple-stranded helical structure is partially disrupted can be prepared. This β-1,3-1,6-glucan can envelop other molecules added into a neutral aqueous solution, and can also envelop molecules that degrade with strongly alkalinity. That is, the present invention discloses an inclusion complex in which a guest molecule is enveloped using at least one of the β-1,3-1,6-glucan powder of the present invention and the glucan-containing composition of the present invention.

The guest molecule is not particularly limited as long as it is a compound capable of being enveloped in β-1,3-1,6-glucan, but ordinarily, one or more of poorly water-soluble substances can be used including a poorly water-soluble vitamin and derivatives thereof, carotenoids and derivatives thereof, terpenes and derivatives thereof, fatty acids and derivatives thereof, polyphenols and derivatives thereof, poorly water-soluble drugs and derivatives thereof, poorly water-soluble staining agents and derivatives thereof, poorly water-soluble carbon materials and derivatives thereof, poorly water-soluble electrically conductive polymers and derivatives thereof, poorly water-soluble nanoparticles, and poorly water-soluble pigments and derivatives thereof.

The present invention also discloses a method for producing an inclusion complex, the method including enveloping a guest molecule using at least one of the β-1,3-1,6-glucan powder of the present invention or the composition of the present invention.

The β-1,3-1,6-glucan powder of the present invention can also be used to recover guest molecules. More specifically, the method for recovering a guest molecule includes enveloping a guest molecule using at least one of the β-1,3-1,6-glucan powder of the present invention or the composition of the present invention.

In the present invention, to further increase the capability to envelop guest molecules, enveloping techniques described in JP 2016-183120 A and JP 2016-113381 A may be also employed, the contents of which are incorporated in the present specification.

The inclusion complex of the present invention can envelop a guest molecule by merely adding the guest molecule to the β-1,3-1,6-glucan. Furthermore, β-1,3-1,6-glucan is approved as a food additive and thus can be utilized in foods without application for new authorization.

In addition to food products, β-1,3-1,6-glucan is also preferably used in pharmaceutical products, cosmetic products, and the like.

EXAMPLE(S)

The present invention is described more specifically below through examples. The materials, usage amounts, proportions, processing contents, processing procedures, and the like described in the examples below may be changed, as appropriate, as long as there is no deviation from the spirit of the present invention. Therefore, the scope of the present invention is not limited to the specific examples described below.

Note that unless otherwise noted, the following experiments were performed in a 25° C. atmosphere.

β-1,3-1,6-Glucan

In Examples 1 to 4, the following glucans were used.

Example 1

β-1,3-1,6-glucan derived from *Aureobasidium pullulans*

Example 2

β-1,3-1,6-glucan (schizophyllan) derived from Schizophyllum commune:

A β-1,3-1,6-glucan having a main chain of β-1,3-glucan and one β-1,6-monoglucoside branch chain for every three glucoses of the main chain

Example 3

β-1,3-1,6-glucan (laminarin) derived from kelp:
The main chain is primarily β-1,3-glucan, and includes partially portions where β-1,6-bonds are formed. In addition, it is thought that the β-1,3-1,6-glucan has branch points and intrasaccharide crosslinking of β-1,6-bonds.

Example 4

β-1,3-1,6-glucan (scleroglucan) derived from sclerotium:
A β-1,3-1,6-glucan having a main chain of β-1,3-glucan and one β-1,6-monoglucoside branch chain for every three glucoses of the main chain Cultivation and Extraction of β-1,3-1,6-Glucan An aqueous culture medium (3 L) containing 10% by mass of D-sucrose, 0.24% by mass of potassium nitrate, 0.12% by mass of dipotassium hydrogen phosphate, 0.06% by mass of potassium chloride, 0.05% by mass of magnesium sulfate heptahydrate, 0.12% by mass of iron sulfate (II) heptahydrate, 0.40% by mass of L-ascorbic acid, and 0.02% by mass of yeast extract (Mist P1G, available from Asahi Group Foods, Ltd.) was prepared in a mini jar fermenter (available from Sanki Seiki Co., Ltd.) equipped with a 5 L flask, a solution of *Aureobasidium pullulans* that had been seed-cultured in advance was added thereto, and the mixture was cultured for seven days at 27° C.

The resulting culture solution was diluted four times with distilled water, the bacterial cells were separated by filtration using a Büchner funnel (No. 5C available from Advantec Co., Ltd.), and the filtrate was added dropwise to ethanol and re-precipitated. After washing the obtained solid with ethanol, water was added, the mixture was lyophilized, and 24.5 g of a white β-1,3-1,6-glucan powder was obtained. The resulting powder is referred to as β-1,3-1,6-glucan powder (derived from *Aureobasidium pullulans*).

Reduction of Molecular Weight of β-1,3-1,6-Glucan through Ultrasonic Decomposition 300 mL of distilled water was added to 200 mg of a β-1,3-1,6-glucan powder (derived from *Aureobasidium pullulans*) and then heated in microwave and dissolved as much as possible. The insoluble matter was then removed by centrifugation (Avanti J-E (available from BECKMAN COULTER), 14000 rpm, 30 min, 25° C.), and a β-1,3-1,6-glucan solution was thereby prepared. The resulting β-1,3-1,6-glucan solution was transferred to a 500 mL beaker, a probe horn of a probe-type ultrasonic irradiator (UH-50, available from As One Corporation) was inserted into the solution, and the solution was ultrasonically irradiated at room temperature for 25 hours.

Insoluble matter suspended in the obtained β-1,3-1,6-glucan solution was removed through centrifugation (Avanti J-E (available from BECKMAN COULTER), 14000 rpm, 30 min, 25° C.), after which the solution was lyophilized, and a low molecular weight β-1,3-1,6-glucan powder (hereinafter, referred to as "β-1,3-1,6-glucan powder (low molecular weight)") was obtained.

The molecular weight of the obtained β-1,3-1,6-glucan powder (low molecular weight) was measured through gel exclusion chromatography (carrier: TOYOPEARL HW-65F, eluent: 0.7 M aqueous sodium hydroxide solution, molecular weight standard: pullulan (P-82, available from Shodex)), and the weight average molecular weight (Mw)=84000, the number average molecular weight (Mn)=2500, and Mw/Mn=33.5.

In addition, the molecular weight of the β-1,3-1,6-glucan powder (derived from *Aureobasidium pullulans*) prior to the ultrasonic irradiation treatment was Mw=3470000, Mn=254000, and Mw/Mn=13.7. This molecular weight was calculated in terms of pullulan for the single-stranded β-1,3-1,6-glucan in the alkali solution. Furthermore, with regard to the molecular weights of the other β-1,3-1,6-glucans used in the experiment, for scleroglucan (PS135, available from Funakoshi Co., Ltd.), the values were Mw=2300000, Mn=58300, and Mw/Mn=39.4; with laminarin (L9634, available from Sigma), the values were Mw=372000, Mn=283000, and Mw/Mn=1.32; and for schizophyllan (catalog number Tlrl-spg, available from Nacalai Tesque), the values were Mw=675000, Mn=287000 and Mw/Mn=2.35.

Preparation of Regenerated β-1,3-1,6-Glucan Solution

Regenerated β-1,3-1,6-glucan was prepared according to the method described in paragraphs [0033] and [0034] of JP 2016-113381 A.

A β-1,3-1,6-glucan powder (derived from *Aureobasidium pullulans*) was dissolved in a 1.0 mol/L aqueous sodium hydroxide solution at a concentration of 2.5% by mass, and an aqueous alkaline solution was obtained.

The same volume of 1.0 mol/L hydrochloric acid was slowly added to the obtained aqueous alkaline solution to thereby neutralize the solution, stirring was continued for 7 days at 25° C., and a regenerated β-1,3-1,6-glucan solution was obtained. The resulting solution was subjected to a dialysis membrane (molecular weight 14000 Cut, available from Nippon Medical Science) and dialyzed with distilled water for 24 hours. At this time, the resulting solution (regenerated β-1,3-1,6-glucan solution) was suspended. The concentration (monomer glucose concentration) of the resulting regenerated β-1,3-1,6-glucan solution was determined by a phenol-sulfuric acid method.

The phenol-sulfuric acid method was performed using a 96 well microplate. 50 μL of a sample solution was charged into an ice-chilled 96 well microplate, and 1.2 μL of an aqueous phenol solution prepared at 80% by mass was added thereto. 124 μL of concentrated sulfuric acid was then added thereto, and ice cooling was continued for 10 minutes in the present state. The plate was agitated for 20 seconds at 1300 rpm using a shaking incubator (SI-150) to thereby mix the solution, after which the solution was allowed to stand for 30 minutes at 60° C., and a coloration reaction was advanced. Subsequently, the absorbance at 492 nm was measured with an ultraviolet (UV) plate reader (available from Thermo Fisher Scientific Inc.). A calibration curve (glucose concentration of from 0.5 to 2.5 mmol/L) was created in advance using glucose, and the monomer glucose concentration was calculated from the obtained absorbance.

In addition, for the turbidity, the $OD_{660}$ (transmittance) at a wavelength of 660 nm was measured. In other words, the solution was diluted such that the glucose concentration was 30 mmol/L (0.49% by mass), and then measured, the measurement was converted, and the $OD_{660}$ at a wavelength of 660 nm was calculated.

The same procedures were conducted for Schizophyllan, laminarin, and scleroglucan as β-1,3-1,6-glucans.

The obtained results are summarized in Table 1. With respect to all of the β-1,3-1,6-glucans that were used, regenerated β-1,3-1,6-glucan solutions could be obtained at monomer glucose concentrations of from 40 to 60 mmol/L, independent of the structure of β-1,3-1,6-glucan. However, suspension was confirmed with all of the regenerated β-1,3-1,6-glucan solutions.

TABLE 1

| Origin of β-1,3-1,6-Glucan | Glucose Concentration | $OD_{660}$ (Transmittance) |
|---|---|---|
| Example 1 *Aureobasidium pullulans* | 46.6 mmol/L | 0.16 (69%) |
| Example 2 Schizophyllan | 40.6 mmol/L | 0.02 (95%) |
| Example 3 Laminarin | 55.9 mmol/L | 0.01 (98%) |
| Example 4 Scleroglucan | 52.1 mmol/L | 0.03 (93%) |

Preparation of Centrifugally Regenerated β-1,3-1,6-Glucan Solutions

The insoluble matter contained in each of the regenerated β-1,3-1,6-glucan solutions prepared above was removed by centrifugation (KUBOTA3740 (available from Kubota Manufacturing Co., Ltd.), 14000 G, 120 minutes), and a transparent centrifugally regenerated β-1,3-1,6-glucan solution (centrifugally regenerated β-1,3-1,6-glucan solution) was obtained. The concentration (monomer glucose concentration) of the resulting centrifugally regenerated β-1,3-1,6-glucan solution was determined by the phenol-sulfuric acid method, and for the turbidity, the $OD_{660}$ at 660 nm was measured. In other words, the solution was diluted such that the glucose concentration was 30 mmol/L (0.49% by mass) and then measured, the measurement was converted, and the $OD_{660}$ at a wavelength of 660 nm was calculated.

The obtained results are summarized in Table 2. After the centrifugation, the insoluble matter (microgel formed of glucan) precipitated in the solution, and a transparent solution was obtained. In association therewith, the glucose concentration of the supernatant decreased. In each of the samples, the transparency increased. At this time, it was confirmed that there was no change in the glucose concentration of the supernatant even when the centrifugation was repeated.

TABLE 2

| Origin of β-1,3-1,6-Glucan | Glucose Concentration (Residue Percentage in Supernatant) | $OD_{660}$ (Transmittance) |
|---|---|---|
| Example 1 *Aureobasidium pullulans* | 40.4 mmol/L (87%) | 0.04 (91%) |
| Example 2 Schizophyllan | 34.5 mmol/L (84%) | 0.01 (98%) |
| Example 3 Laminarin | 47.8 mmol/L (86%) | 0.01 (98%) |
| Example 4 Scleroglucan | 42.9 mmol/L (82%) | 0.01 (98%) |

Production of Powder of β-1,3-1,6-Glucan Glucan

Each of the regenerated β-1,3-1,6-glucan solutions and each of the centrifugally regenerated β-1,3-1,6-glucan solutions obtained as described above were lyophilized in a freeze dryer (FDU-1200, available from Tokyo Rikakikai Co., Ltd.), and respective β-1,3-1,6-glucan powders were obtained.

In addition, for the β-1,3-1,6-glucan derived from *Aureobasidium pullulans*, a centrifugally regenerated β-1,3-1,6-glucan solution was formed into a powder through spray drying using a Mini Spray Dryer B-290 (inlet temperature: 160° C., outlet temperature: 80° C.) available from Btichi Labortechnik AG.

Furthermore, β-1,3-1,6-glucan derived from *Aureobasidium pullulans* was also formed into powder through a known method. That is, a 25% by mass aqueous sodium hydroxide solution was added to the culture solution of *Aureobasidium pullulans* such that the final concentration was 2.4% by mass, and the mixture was agitated. Diatomaceous earth was then added thereto at a concentration of 1% by mass, and the bacterial cells were separated by filtration using a Büchner funnel. A 50% by mass aqueous citric acid solution was added to the obtained filtrate, and the pH was adjusted to 3.5, after which the mixture was re-precipitated with ethanol. At this time, the final concentration of ethanol was 66 vol. %, and the generated solid was washed with ethanol, after which distilled water was added thereto, the mixture was lyophilized, and a known method was used to obtain β-1,3-1,6-glucan powder.

Solubility of β-1,3-1,6-Glucan Powder

The following experiments were conducted to examine the re-solubility in water for each of the obtained β-1,3-1,6-glucan powders.

10 mg of each β-1,3-1,6-glucan powder obtained as described above was placed in a 1.5 mL plastic tube, and 1 mL of distilled water was added thereto (at a concentration of 1.0% by mass), and then stirred with a vortex mixer for 5 minutes to dissolve as much as possible (stirring was continued for up to 30 minutes for hardly dissolved powder). A centrifugation (Micro-12 High Speed Micro Centrifuge (available from Greiner Bio-One GmbH), 15000 rpm, 5 minutes) was performed to remove undissolved β-1,3-1,6-glucan, the supernatant was removed, and the concentration of the dissolved β-1,3-1,6-glucan (monomer glucose concentration) was calculated from the phenol-sulfuric acid method. At the same time, assuming that all 10 mg of the powder was glucan, the dissolution ratio (the percentage of the β-1,3-1,6-glucan powder that was dissolved, unit: % by mass) was calculated.

The obtained results are summarized in Table 3. From Table 3, the results indicated that for the β-1,3-1,6-glucan powder that was pulverized by a known method, 10 mg of β-1,3-1,6-glucan powder added hardly dissolved and was precipitated as a solid, the glucan solubility was only 22% by mass, and the $OD_{660}$ was a high value of 0.28. On the other hand, for the β-1,3-1,6-glucan prepared according to the method of the present invention, a dissolution ratio of 70% by mass or higher was exhibited, and almost no precipitate could be confirmed. The $OD_{660}$ was also 0.04 or less, and in the present invention, a β-1,3-1,6-glucan powder with very high re-solubility could be obtained with a higher glucan concentration than that of the related art.

As the sample solutions used for dynamic light scattering measurements, regenerated β-1,3-1,6-glucan prepared with β-1,3-1,6-glucan derived from *Aureobasidium pullulans*, a solution of centrifugally regenerated β-1,3-1,6-glucan, and a solution in which β-1,3-1,6-glucan powder was re-dissolved were used, and the solutions were measured at 25° C. Each β-1,3-1,6-glucan solution was diluted such that the monomer glucose concentration (measured by the phenol-sulfuric acid method) was adjusted to 10 mmol/L.

Dynamic light scattering measurements were performed using β-1,3-1,6-glucan dissolved in distilled water. Specifically, each measurement was implemented under the following conditions: refractive index of β-1,3-1,6-glucan: 1.673, glucan absorbance (633 nm): 0.01, temperature of the dispersion medium (water): 25° C., viscosity of the dispersion medium: 0.8872 cP, refractive index of the dispersion medium: 1.33, equilibration time: 120 seconds, number of scans: 10 scans, and measurement time: 10 seconds. This measurement was repeated 10 times, and the obtained data was averaged and used as the result.

The results are shown in FIG. 1 and Table 4 below. The horizontal axis shows the particle size and the vertical axis shows the volume fraction. The dashed line indicates the regenerated β-1,3-1,6-glucan before lyophilization, and the solid line indicates the centrifugally regenerated β-1,3-1,6-glucan before lyophilization. From FIG. 1, it is clear that large particles having a particle size of 1000 nm or more (1 μm or more) were present in the sample before centrifugation, but when subjected to centrifugation, the large particles were removed, and the particle size became less than 100 nm (around several tens of nm).

Figure 2:
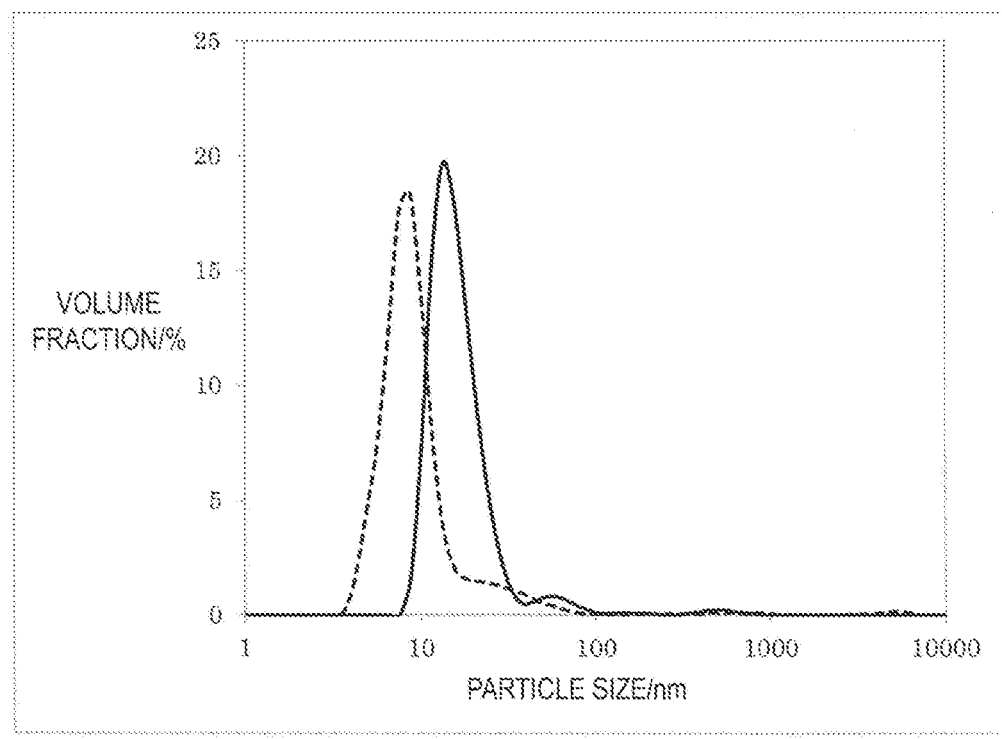
FIG. 2 is a graph illustrating the distribution of particle sizes of the β-1,3-1,6-glucan prepared in the examples after lyophilization.

It was also found that when centrifugally regenerated β-1,3-1,6-glucan that had been lyophilized was used, the particle size was smaller than before lyophilization (FIG. 2, Table 4). The solid line indicates the centrifugally regenerated β-1,3-1,6-glucan before lyophilization, and the dashed line indicates the centrifugally regenerated β-1,3-1,6-glucan after lyophilization. For example, for the regenerated β-1,3-1,6-glucan, the peak in volume fraction centered on a particle size of 51.3 nm shifted to a peak in volume fraction

TABLE 3

| | | Preparation Method | Glucose Concentration (Dissolution Ratio %) | $OD_{660}$ |
|---|---|---|---|---|
| Example 1 | β-1,3-1,6-glucan derived from *Aureobasidium pullulans* | Regenerated β-1,3-1,6-glucan | 54.9 mmol/L (89%) | 0.04 |
| | | Lyophilization | 51.8 mmol/L (84%) | 0.02 |
| | | Spray dried powder | 51.2 mmol/L (83%) | 0.02 |
| Comparative Example 1 | | Glucan powder (known method) | 13.7 mmol/L (22%) | 0.28 |
| Example 2 | Schizophyllan | Lyophilization | 50.6 mmol/L (82%) | 0.02 |
| Example 3 | Laminarin | Lyophilization | 51.1 mmol/L (83%) | 0.01 |
| Example 4 | Scleroglucan | Lyophilization | 47.8 mmol/L (78%) | 0.02 |

As shown in Table 3 above, with each of the centrifugally regenerated β-1,3-1,6-glucans, β-1,3-1,6-glucan powders with high re-solubility could be obtained. This is believed to be due to the removal of particles with a large particle size by centrifugation.

Therefore, the difference in turbidity of the β-1,3-1,6-glucan solution occurring before and after centrifugation was compared by measuring the change in particle size by dynamic light scattering measurements (Zetasizer Nano ZS, available from Malvern Panalytical Ltd.).

centered on a particle size of 25.6 nm, and the peak in volume fraction centered on a particle size of 1176 nm shifted to a peak in volume fraction centered on a particle size of 817.7 nm. For the centrifugally regenerated β-1,3-1,6-glucan as well, the peak in volume fraction centered on a particle size of 16.0 nm shifted to a peak in volume fraction centered on a particle size of 11.3 nm (FIG. 2). In addition, for the centrifugally regenerated β-1,3-1,6-glucan, glucan with a large particle size was not produced even when the lyophilized powder was redissolved.

TABLE 4

|  | Volume Fraction Peak of Particle Size Before Lyophilization | Volume Fraction Peak of Particle Size After Lyophilization |
| --- | --- | --- |
| Regenerated β-1,3-1,6-glucan | 15.6 nm, 51.3 nm, 1176 nm | 25.6 nm, 124 nm, 817.7 nm |
| Centrifugally regenerated β-1,3-1,6-glucan | 16.0 nm, 60.4 nm | 11.3 nm | the centrifugally regenerated β-1,3-1,6-glucan solution cannot be obtained, and a maximum glucan concentration of only 0.8% by mass can be obtained. However, when the method for powder formation according to the present invention is conducted, and the powder is re-dissolved, the glucan concentration can be increased to 5.0% by mass (6 times the concentration in the known method). That is, a solution with a high concentration of glucan, which could not be typically produced, can be prepared in association with powder formation.

TABLE 5

| % by mass Concentration After Neutralization (including insoluble matter) | % by mass Concentration of Centrifugally Regenerated β-1,3-1,6-Glucan | Solution Properties After Neutralization and Dialysis |
| --- | --- | --- |
| 0.005% | 0.003% (0.2 mmol/L) | Suspension |
| 0.05% | 0.03% (1.9 mmol/L) | Suspension |
| 0.25% | 0.2% (12 mmol/L) | Suspension |
| 0.5% | 0.4% (23 mmol/L) | Suspension |
| 1.25% | 0.8% (50 mmol/L) | Suspension |
| 2.5% | ※ | Gelled |

※ The solution gelled, and the supernatant solution could not be extracted even with centrifugation.

Saturation Solubility of Centrifugally Regenerated β-1,3-1,6-Glucan Powder

As noted above, the centrifugally regenerated β-1,3-1,6-glucan powder prepared according to the method of the present invention exhibited higher solubility than the β-1,3-1,6-glucan powder obtained by a known method.

Therefore, the saturation solubility at 25° C. was measured using β-1,3-1,6-glucan powder derived from *Aureobasidium pullulans*.

Here, as the β-1,3-1,6-glucan powder that was used, centrifugally regenerated β-1,3-1,6-glucan powder was used in addition to centrifugally regenerated β-1,3-1,6-glucan powder (low molecular weight) converted to low molecular weight by ultrasound irradiation, and the operation was carried out as follows.

An operation of adding 1 mg of centrifugally regenerated β-1,3-1,6-glucan powder to a 1.5 mL plastic tube containing 200 μL of distilled water, and stirring in a vortex mixer for 5 minutes was continued as long as the added powder remained dissolved, and a total amount of up to 10 mg was dissolved, but at 11 mg, the powder did not dissolve. When the same experiment was carried out with the centrifugally regenerated β-1,3-1,6-glucan powder (low molecular weight), saturation occurred at a total amount of 20 mg.

The obtained results indicate that the saturation solubility of the centrifugally regenerated β-1,3-1,6-glucan powder was 5.0% by mass, and the saturation solubility of the centrifugally regenerated β-1,3-1,6-glucan powder (low molecular weight) was 10.0% by mass, and that when the molecular weight is reduced, the saturation solubility increases.

Furthermore, Table 5 below shows the concentration of the centrifugally regenerated β-1,3-1,6-glucan prior to lyophilization. When the concentration of glucan dissolved in the alkaline solution increases, the solution becomes gelled, Experiment for Inclusion of Poorly Water-Soluble Substance (Preparation of Inclusion Complex)

In order to examine the change in characteristics of centrifugally regenerated β-1,3-1,6-glucan in association with powder formation, the envelopment and solubilizing capacity of the centrifugally regenerated β-1,3-1,6-glucan with respect to poorly water-soluble substances were compared.

β-1,3-1,6-glucan (lyophilized) derived from *Aureobasidium pullulans* was used as the centrifugally regenerated β-1,3-1,6-glucan powder, and curcumin (available from Tokyo Chemical Industry Co., Ltd., catalog number: 00435) was used as the poorly water-soluble substance.

The centrifugally regenerated β-1,3-1,6-glucan powder was dissolved in distilled water at a concentration of 1.0% by mass, and the glucose concentration was calculated through the phenol-sulfuric acid method, after which the solution was diluted and used. A centrifugally regenerated β-1,3-1,6-glucan solution prior to powder formation was used as a control for examining the change in the enveloping capacity through powder formation, and the solution was similarly diluted and used in the experiment.

Each centrifugally regenerated β-1,3-1,6-glucan solution having a monomer glucose concentration adjusted to 0.002 mol/L was prepared at an amount of 1 mL each, and an acetone solution of curcumin adjusted to a concentration of 0.05 mol/L was added such that the final concentration of acetone was 1 vol. %. At this time, a shaking incubator (SI-150, available from As One Corporation) was used to shake and agitate the solution for 3 hours at 25° C. and 1300 rpm in order to precipitate the unenveloped curcumin. Centrifugation (KUBOTA3740 (available from Kubota Manufacturing Co., Ltd.), 14000 G, 5 minutes) was carried out, the insoluble matter was removed, and the absorbance of the supernatant at a wavelength of 405 nm was compared. The unenveloped curcumin was removed through centrifugation, and therefore the absorbance originated from the curcumin that was enveloped and solubilized by the centrifugally regenerated β-1,3-1,6-glucan.

Figure 3:
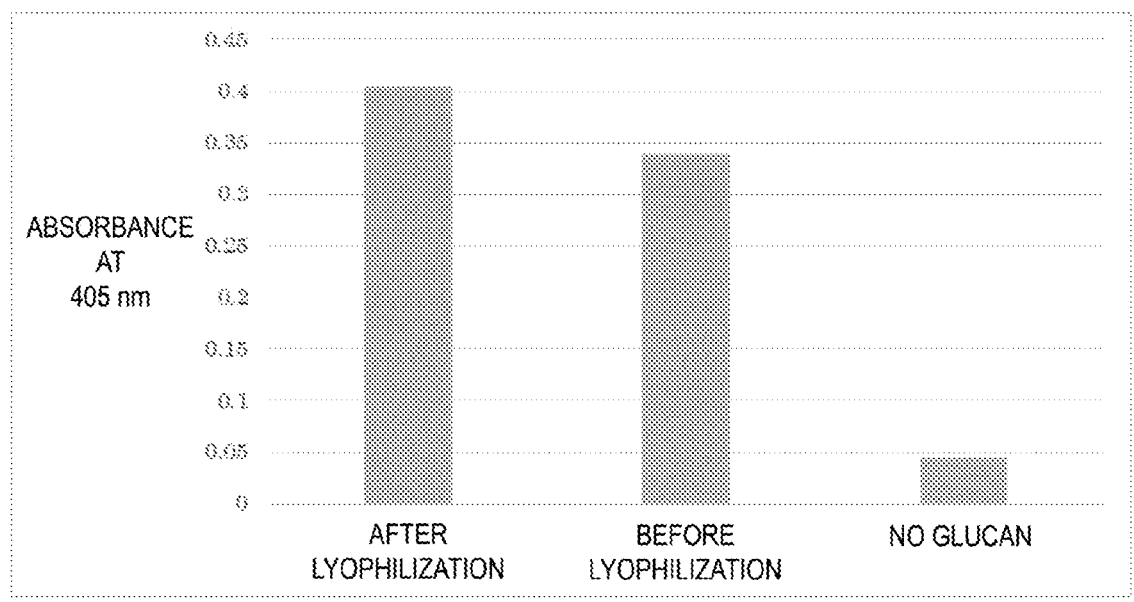
FIG. 3 is a graph illustrating the absorbance of a β-1,3-1,6-glucan inclusion complex in which curcumin is enveloped, and the absorbance of non-enveloped curcumin (without glucan), both prepared in the examples.

As illustrated in FIG. 3, the absorbance (wavelength of 405 nm) originating from the curcumin in the supernatant was 0.045 in the absence of β-1,3-1,6-glucan, was 0.340 with the regenerated β-1,3-1,6-glucan solution not yet subjected to lyophilization, was 0.404 (18% increase) with the solution (lyophilized) derived from the regenerated β-1,3-1,6-glucan powder, and was 0.138 with a solution derived from (spray dried) β-1,3-1,6-glucan powder of a solution derived from regenerated β-1,3-1,6-glucan powder. With the centrifugally regenerated β-1,3-1,6-glucan powder subjected to lyophilization, it is clear that the enveloping capacity with respect to curcumin is improved.

Powder Formation and Saturation Solubility of Inclusion Complex 0.20 mL of an acetone solution of curcumin adjusted to a concentration of 0.05 mol/L was added to 20 mL of a regenerated β-1,3-1,6-glucan powder solution adjusted to a concentration of 30 mM, such that the final concentration of acetone was 1 vol. %. The mixture was stirred for 5 minutes with a vortex mixer in order to precipitate the unenveloped curcumin. Centrifugation (KUBOTA3740 (available from Kubota Manufacturing Co., Ltd.), 14000 G, 5 minutes) was carried out, the insoluble matter was removed, the supernatant was lyophilized, and 80 mg of a yellow colored powder was obtained.

The saturation solubility of the obtained powder of the curcumin/centrifugally regenerated β-1,3-1,6-glucan complex was measured. An operation of adding 1 mg of the curcumin/centrifugally regenerated β-1,3-1,6-glucan complex powder to a 1.5 mL plastic tube containing 200 µL of distilled water, and stirring in a vortex mixer for 5 minutes was continued as long as the added powder remained dissolved, and saturation was reached at a total amount of 10 mg.

The obtained results indicated that there was no difference with the saturation solubility of the centrifugally regenerated β-1,3-1,6-glucan powder (β-1,3-1,6-glucan not enveloping a poorly water-soluble substance) obtained as described above, and therefore it was clear that regardless of whether a poorly water-soluble substance is enveloped or not enveloped, a difference is not made in the saturation solubility of the obtained β-1,3-1,6-glucan powder.

Comparison of Saturation Solubility to Curcumin

In order to evaluate the level of the solubility of the curcumin/β-1,3-1,6-glucan complex powder prepared as described above, the absorbance was compared with that of a solution containing curcumin. In the experiment, a solution of the curcumin/centrifugally regenerated β-1,3-1,6-glucan complex solution obtained as described above from curcumin (available from Tokyo Chemical Industry Co., Ltd., catalog number: C0435); a saturated solubility solution obtained from a powder of a curcumin/centrifugally regenerated β-1,3-1,6-glucan complex prepared by lyophilizing the curcumin/centrifugally regenerated β-1,3-1,6-glucan complex solution; a solution obtained by using a vortex mixer to maximally dissolve 10 mg of a 100% by mass Autumn turmeric powder (available from Orihiro Co., Ltd.) in 1 mL of water; and a solution of commercially available product of Ukon no Chikara (trade name, available from House Wellness Foods Co., Ltd.) were each used.

Figure 4:
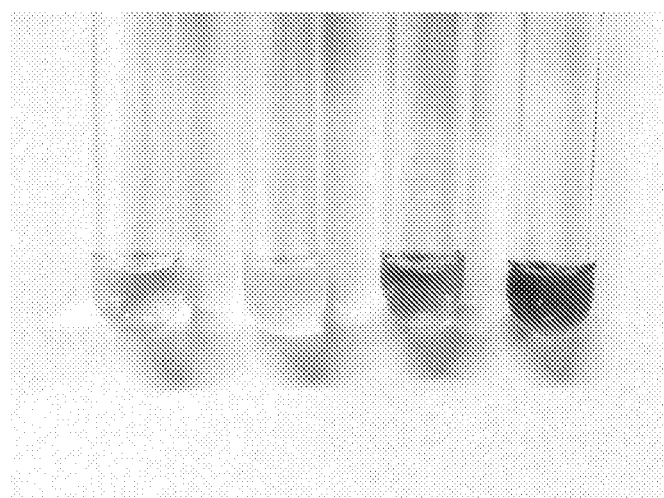
FIG. 4 is a photograph of solutions prepared in the examples.

FIG. 4 shows a photograph of the solutions. From the left, the saturated solutions obtained from the 100% by mass Autumn turmeric powder, the Ukon no Chikara, the curcumin/centrifugally regenerated β-1,3-1,6-glucan complex solution, and the curcumin/centrifugally regenerated β-1,3-1,6-glucan complex powder, are shown, and it is clear that solubility of the solution prepared from the powder according to the present invention is high.

The curcumin solubility with respect to the 100% by mass Autumn turmeric powder was estimated from the absorbance (440 nm) of the supernatant shown in Table 6, and the Ukon no Chikara was found to exhibit solubility of 15 times, and the curcumin/centrifugally regenerated β-1,3-1,6-glucan complex solution was found to exhibit solubility of 143 times, whereas the saturated solution obtained from the curcumin/centrifugally regenerated β-1,3-1,6-glucan complex powder according to the present invention exhibited solubility that was improved up to 1320 times. Even compared to the curcumin/centrifugally regenerated β-1,3-1,6-glucan complex solution not formed into a powder, the solubility of the saturated solution obtained from the powder according to the present invention was high, namely 9.2 times that of the complex solution not formed into a powder.

Note that for the diluted and measured samples, values obtained by multiplying the dilution ratio by the absorbance measured after dilution are presented.

TABLE 6

| | Autumn Turmeric Powder | Ukon no Chikara | Centrifugally regenerated β-1,3-1,6-glucan/curcumin complex solution | Solution obtained by redissolving centrifugally regenerated β-1,3-1,6-glucan/curcumin complex powder |
|---|---|---|---|---|
| $Abs_{440}$ | 0.166 | 2.45 | 23.7 | 219 |

Stability of Inclusion Complex

The release behavior (envelopment stability) of the enveloped curcumin was compared using the curcumin/centrifugally regenerated β-1,3-1,6-glucan complex solution and the curcumin/centrifugally regenerated β-1,3-1,6-glucan complex powder prepared above. 3 mg of the curcumin/centrifugally regenerated β-1,3-1,6-glucan complex powder was measured and dissolved in 5 mL of distilled water, and the obtained solution was used.

The stability of the obtained solution was determined by leaving the solution in a constant temperature incubator set to 40° C., and then measuring the absorbance (wavelength: 405 nm) of the supernatant at fixed time intervals using a microplate reader. Curcumin exhibits low water-solubility and precipitates when released from β-1,3-1,6-glucan, and therefore the absorbance decreases. That is, as the absorbance decreases, the complex becomes more unstable.

Figure 5:
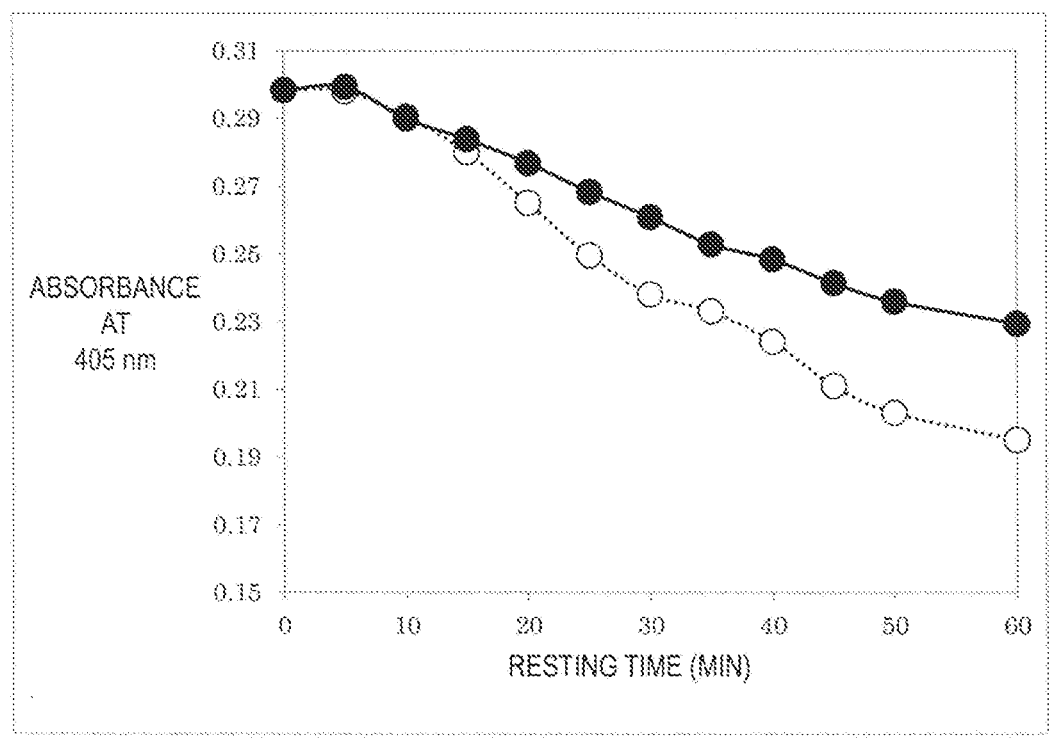
FIG. 5 is a graph illustrating the stability over time of a β-1,3-1,6-glucan inclusion complex in which curcumin was enveloped and which was prepared in the examples.

From the obtained results, for example, at 40° C., with the curcumin/centrifugally regenerated β-1,3-1,6-glucan complex solution (white circles in FIG. 5), after 1 hour, 45% by mass of the curcumin had been released, whereas with the solution in which the curcumin/centrifugally regenerated β-1,3-1,6-glucan complex powder was redissolved (black circles in FIG. 5), the release of curcumin was limited to 30% by mass after 1 hour. When the half-life was calculated from the release rate, it was found that the half-life of the curcumin/centrifugally regenerated β-1,3-1,6-glucan complex solution is 1.6 hours, and the half-life of the curcumin/centrifugally regenerated β-1,3-1,6-glucan complex powder is 2.2 hours, and it was found that the stability clearly increased (FIG. 5). The improved thermal stability in association with this powder formation similarly occurs at temperatures other than 40° C., and thus the improved thermal stability can be said to be a functional improvement associated with powder formation.

Effect of Powder Formation with Respect to other Poorly Water-Soluble Substances Furthermore, with respect to the inclusion complex described above, it was confirmed that the present invention exhibits a similar trend when curcumin is replaced with resveratrol and β-carotene, and the same operations are implemented.

INDUSTRIAL APPLICABILITY

Through the present invention, a β-1,3-1,6-glucan powder with high solubility in water can be obtained, and high concentration solutions can be provided even with poorly water-soluble guest molecules and the like.

The invention claimed is:

1. A β-1,3-1,6-glucan powder with a saturation solubility in water at 25° C. of from 1.0 to 20.0% by mass,
   wherein in a particle size distribution of β-1,3-1,6-glucans, determined by subjecting the β-1,3-1,6-glucan powder to dynamic light scattering measurements, a particle size of a peak representing a largest volume fraction is in a range of from 5 nm to less than 100 nm, and a volume fraction of a peak outside of the particle size range of from 5 nm to less than 100 nm is 30% or less of the volume fraction of the peak having the largest volume fraction.

2. A β-1,3-1,6-glucan powder wherein,
   in a particle size distribution of β-1,3-1,6-glucans, determined by subjecting the β-1,3-1,6-glucan powder to dynamic light scattering measurements, a particle size of a peak representing a largest volume fraction is in a range of from 5 nm to 15 nm, and a volume fraction of a peak outside of the particle size range of from 5 nm to 15 nm is 30% or less of the volume fraction of the peak having the largest volume fraction.

3. A glucan-containing composition comprising water and β-1,3-1,6-glucans, wherein
   the β-1,3-1,6-glucans are dissolved at a ratio of from 1.0 to 20.0% by mass in water; and
   in a particle size distribution of β-1,3-1,6-glucans, determined by subjecting the composition to dynamic light scattering measurements, a particle size of a peak representing a largest volume fraction is in a range of from 5 nm to less than 100 nm, and a volume fraction of a peak outside of the particle size range of from 5 nm to 15 nm is 30% or less of the volume fraction of the peak having the largest volume fraction.

4. A β-1,3-1,6-glucan-containing composition comprising water and β-1,3-1,6-glucans, wherein,
   in a particle size distribution of β-1,3-1,6-glucans, determined by subjecting the glucan-containing composition to dynamic light scattering measurements, a particle size of a peak representing a largest volume fraction is in a range from 5 nm to 15 nm, and a volume fraction of a peak outside of the particle size range from 5 nm to 15 nm is 30% or less of the volume fraction of the peak having the largest volume fraction.

5. A glucan-containing composition comprising the β-1,3-1,6-glucan powder described in claim 1, and water.

6. The glucan-containing composition according to claim 5, wherein the composition has a transmittance of light with a wavelength of 660 nm at 25° C. of 70% or more.

7. An inclusion complex in which a guest molecule is enveloped in β-1,3-1,6-glucan derived from a β-1,3-1,6-glucan powder according to claim 1 with a saturation solubility in water at 25° C. of from 1.0 to 20.0% by mass.

8. The inclusion complex according to claim 7, wherein the inclusion complex is in powder form.

9. An inclusion complex in which a guest molecule is enveloped in β-1,3-1,6-glucan derived from the β-1,3-1,6-glucan powder described in claim 5.

10. A method for producing an inclusion complex, the method comprising enveloping a guest molecule using the β-1,3-1,6-glucan powder described in claim 1.

11. The method for producing an inclusion complex according to claim 10, wherein the inclusion complex is in powder form.

12. A method for recovering a guest molecule, the method comprising enveloping a guest molecule using the β-1,3-1,6-glucan powder described in claim 1.

13. A method for recovering a guest molecule, the method comprising enveloping a guest molecule using the β-1,3-1,6-glucan powder described in claim 5.

14. A method for producing an inclusion complex, the method comprising enveloping a guest molecule using the β-1,3-1,6-glucan powder described in claim 5.

* * * * *